(12) United States Patent  
Latkany et al.

(10) Patent No.: US 12,396,734 B1  
(45) Date of Patent: Aug. 26, 2025

(54) DEVICES AND METHODS FOR OCCLUDING THE PUNCTAL OPENING

(71) Applicant: Oasis Medical, Inc., Glendora, CA (US)

(72) Inventors: Robert Latkany, New York, NY (US); James Marlow Christensen, Glendora, CA (US)

(73) Assignee: Oasis Medical, Inc., Glendora, CA (US)

( * ) Notice: Subject to any disclaimer, the term of this patent is extended or adjusted under 35 U.S.C. 154(b) by 167 days.

(21) Appl. No.: 17/017,529

(22) Filed: Sep. 10, 2020

(51) Int. Cl.  
*A61B 17/12* (2006.01)

(52) U.S. Cl.  
CPC .. *A61B 17/12159* (2013.01); *A61B 17/12031* (2013.01); *A61B 17/12099* (2013.01)

(58) Field of Classification Search  
CPC ........ A61B 17/12159; A61B 17/12099; A61B 17/12022; A61B 17/1204; A61B 17/0057; A61B 17/12031; A61B 17/12036; A61B 17/12045; A61B 17/12172; A61B 17/12; A61F 9/00772; A61F 9/00781; A61F 9/00; A61F 9/007; A61F 9/0017; A61F 9/0026; A61F 9/0008; A61K 9/0051  
USPC ...................................... 128/887; 604/8, 294  
See application file for complete search history.

(56) References Cited

U.S. PATENT DOCUMENTS

| | | | | |
|---|---|---|---|---|
| 3,949,750 A | * | 4/1976 | Freeman | A61F 9/00772 606/107 |
| 4,959,048 A | | 9/1990 | Seder et al. | |
| 5,049,142 A | * | 9/1991 | Herrick | A61F 9/00772 604/11 |
| 5,163,959 A | * | 11/1992 | Herrick | A61F 9/00772 623/905 |
| 5,334,137 A | * | 8/1994 | Freeman | A61B 17/12022 604/8 |

(Continued)

FOREIGN PATENT DOCUMENTS

| | | |
|---|---|---|
| EP | 1629800 | 3/2006 |
| WO | WO 2015/006999 | 1/2015 |

OTHER PUBLICATIONS

International Search Report and Written Opinion for Application No. PCT/US2021/049136 dated Dec. 10, 2021, 24 pages.

(Continued)

*Primary Examiner* — Alireza Nia  
*Assistant Examiner* — Robin Han  
(74) *Attorney, Agent, or Firm* — Knobbe, Martens, Olson & Bear, LLP (57) ABSTRACT

Disclosed herein are embodiments of a plug for occluding the lacrimal drainage system. The plug can have a body portion having a first end and a second end, a tapered portion extending away from the second end of the body portion, the tapered portion having a conical shape, and a rounded distal tip. The body portion can have a continuous cylindrical shape between the first end and the second end thereof, and can be shaped such that the first end is planar and is orthogonal to a plug's longitudinal axis. Additionally, in some embodiments, the plug can be configured to occlude a vertical canaliculi of the lacrimal drainage system. For example and without limitation, some embodiments of the plug can be configured to be inserted completely within the vertical canaliculi of the lacrimal drainage system so that no portion extends outside of punctal opening.

17 Claims, 7 Drawing Sheets

(56) References Cited

U.S. PATENT DOCUMENTS

| | | | |
|---|---|---|---|
| 6,082,362 A | 7/2000 | Webb | |
| 6,306,114 B1* | 10/2001 | Freeman | A61F 9/00772 |
| | | | 604/9 |
| 7,404,825 B2* | 7/2008 | Herrick, II | A61B 17/12159 |
| | | | 623/4.1 |
| 7,862,532 B2* | 1/2011 | Murray | A61F 9/00772 |
| | | | 604/9 |
| 8,090,426 B2* | 1/2012 | Felder | A61B 5/1486 |
| | | | 600/347 |
| 9,320,526 B1 | 4/2016 | Mendius et al. | |
| 9,421,127 B2* | 8/2016 | Lust | A61M 31/002 |
| 2002/0198453 A1 | 12/2002 | Herrick | |
| 2005/0283109 A1* | 12/2005 | Peyman | A61F 9/00772 |
| | | | 604/8 |
| 2007/0299516 A1* | 12/2007 | Cui | A61F 9/0017 |
| | | | 623/4.1 |
| 2010/0209477 A1 | 8/2010 | Butuner et al. | |
| 2011/0196317 A1* | 8/2011 | Lust | A61B 50/30 |
| | | | 604/290 |
| 2018/0201426 A1* | 7/2018 | Witham | B65D 79/00 |
| 2018/0289543 A1* | 10/2018 | Silverberg | A61L 31/148 |
| 2021/0283316 A1* | 9/2021 | Lu | A61F 9/00781 |

OTHER PUBLICATIONS

Oasis: "Soft Plug Punctum Plug Silicone", Dec. 31, 2019 (Dec. 31, 2019), pp. 1-2, Retrieved from the Internet: URL: https://oasismedical.com/docs/default-source/resources/softplugsiliconeplug-ifu.pdf; Section "Insertion".

Lacrimedics Products, dated as available at https://www.lacrimedics.com/products on Aug. 8, 2020 by the Wayback Machine internet archive (accessed and printed on Mar. 8, 2021); 3 pages.

Dry Eye Doctor, Dr. Robert Latkany & Dr. Evelyn Icasiano, Punctual Plugs, dated as available at https://dryeyedoctor.com/punctal-plugs/ on Aug. 15, 2020 by the Wayback Machine internet archive (accessed and printed on Mar. 8, 2021); 4 pages.

Mayo Clinic, Punctual Plugs; dated as available at https://www.mayoclinic.org/diseases-conditions/dry-eyes/multimedia/punctal-plugs/img-20007894 on Aug. 10, 2020 by the Wayback Machine internet archive (accessed and printed on Mar. 8, 2021); 2 pages.

* cited by examiner

DEVICES AND METHODS FOR OCCLUDING THE PUNCTAL OPENING

FIELD OF THE DISCLOSURE

Embodiments of the present disclosure relate to occlusion devices for the lacrimal drainage system.

BACKGROUND

Many people suffer from dry eyes. This can occur when a person's eyes do not make enough tears to keep their eyes sufficiently moistened, or when the quality of the tears is insufficient. Eye drops are often used to treat dry eye. However, for some people, plugs inserted into their tear ducts can help them maintain more moisture in their eyes and improve their level of comfort.

Punctal plugs, which are also called punctum plugs, lacrimal plugs or occluders, are tiny devices that can be placed in one or more of the tear ducts of a person's eyes. Tear duct openings, referred to as puncta, are the tiny openings that drain tears from the eyes. By filling or occluding the puncta, punctal plugs essentially stop fluid from draining from the eye. This can help keep the eye's surface moist and comfortable, and can relieve other forms of eye discomfort, such as itchy, burning, and red eyes.

However, conventional punctal plugs suffer from some risks and drawbacks. For example and without limitation, conventional punctal plugs are designed so that a portion of the plug rests on the eyelid outside of the punctum, making such plugs susceptible to inadvertent removal, such as when a user rubs his or her eyes. Further, the head portion of these punctal plugs have shapes that can rub against the cornea or trap cosmetics or other debris which can irritate and/or inflame portions of the ocular tissues that the plug is in contact with. Further, the anchor portion of these punctal plugs are larger than the punctal opening and excessive dilation of the punctum in order to insert the anchor of the plug can cause tearing of the punctal muscle leading to later loss of the plug.

SUMMARY OF SOME EXEMPLIFYING EMBODIMENTS

The systems, methods and devices of this disclosure each have several innovative aspects, implementations, or aspects, no single one of which is solely responsible for the desirable attributes disclosed herein.

Disclosed herein are embodiments of plug devices for occluding the lacrimal drainage system. Some embodiments of the plug devices can have a body portion having a first end and a second end, a tapered portion extending away from the second end of the body portion, and a distal tip at the distal end of the tapered portion. In some embodiments, the tapered portion can have a conical shape and/or the distal tip can be rounded (e.g., to avoid having a sharp edge and inhibit injury to tissue during insertion of the plug). In some embodiments, the body portion can have a continuous cylindrical shape between the first end and the second end thereof, and can be shaped such that the first end is planar (or approximately planar) and is orthogonal (or approximately orthogonal) to a longitudinal axis A of the plug. Any embodiments of the plug device can have a shape that is symmetrical about a longitudinal axis of the plug device.

Additionally, in some embodiments, the plug can be configured to occlude one or more canaliculi of the lacrimal drainage system. For example and without limitation, the plug can be configured to be inserted completely within one or more of the vertical or horizontal canaliculi of the lacrimal drainage system so that no portion extends outside of the punctal opening.

Kit:

Also disclosed herein are embodiments of a kit for occluding an upper canaliculus and a lower canaliculus, or alternatively a left canaliculus and a right canaliculus, including a first plug and a second plug that is a different size than the first plug. In some embodiments, the first plug can have a body portion having a continuous cylindrical outer surface between a first end and a second end thereof, and/or have any of the features, sizes, and/or other details of any of the plug device embodiments disclosed herein. In some embodiments, the outer surface of the first plug can have a first diameter and the first plug can have a tapered portion projecting from the body portion of the first plug in an axial direction. The second plug can have any of the features, sizes, and/or other details of any of the plug device embodiments disclosed herein. For example, some embodiments of the second plug can have a body portion having a continuous cylindrical outer surface between a first end and a second end thereof, the outer surface having a second diameter. The second plug can have a tapered portion projecting from the body portion of the second plug in an axial direction. In some embodiments, a diameter or a cross-sectional size of the second plug can be different than a diameter or a cross-sectional size of the first plug. For example and without limitation, the second diameter or cross-sectional size can be less than the first diameter or cross-sectional size of the first plug. Or, in some embodiments, the second diameter or cross-sectional size can be greater than the first size or diameter of the first plug. Additionally, in some embodiments, the first plug can be removably coupled with a first insertion or delivery device and the second plug can be removably coupled with a second insertion or delivery device so that the first and second plugs are ready to be implanted or inserted upon opening of the kit.

Method:

Also disclosed herein are embodiments of a method of occluding a lacrimal drainage system. In some embodiments, the method can include inserting a first plug through a first punctum of the lacrimal drainage system and into a first vertical canaliculus of the lacrimal drainage system. In some embodiments, the first plug can be inserted through a first punctum and through a first vertical canaliculus into a first horizontal canaliculus of the lacrimal drainage system. In some embodiments, the first plug can have any of the features, sizes, and/or other details of any of the plug device embodiments disclosed herein. For example and without limitation, some embodiments of the first plug can have a body portion having a first end and a second end and a tapered portion extending away from the second end of the body portion. The tapered portion can have a conical shape. In some embodiments, the body portion can have a continuous cylindrical shape between the first end and the second end thereof.

Some embodiments of the method can further include advancing a second plug through a second punctum of the lacrimal drainage system and into a second vertical canaliculus or horizontal canaliculus of the lacrimal drainage system. In some embodiments, the second plug can have any of the features, sizes, and/or other details of any of the plug device embodiments disclosed herein. For example and without limitation, the second plug can have a body portion having a first end and a second end and a tapered portion extending away from the second end of the body portion of the second plug. The tapered portion of the second plug can have a conical shape, and/or can have a rounded distal tip.

Size:

Any embodiments of the devices, kits, and methods disclosed herein can include, in additional embodiments, one or more of the following features, components, and/or details, in any combination with any of the other features, components, and/or details of any other embodiments disclosed herein: wherein the plug is configured to be inserted through a wide range of punctum sizes, for example and without limitation, wherein the plug (for example and without limitation, a single size of the plug) is configured to be inserted through a punctal opening having a diameter of from 0.2 mm (or approximately 0.2 mm) or less to 1.0 mm (or approximately 1.0 mm) or more; wherein the body portion of the plug can have a diameter D1 of 0.6 mm (or approximately 0.6 mm); wherein the body portion of the plug can have a diameter D1 of from 0.3 mm (or approximately 0.3 mm) or less to 0.9 mm (or approximately 0.9 mm) or more, or from 0.5 mm (or approximately 0.5 mm) to 0.7 mm (or approximately 0.7 mm), or of any values within any of the foregoing ranges or from and to any values within the foregoing ranges; wherein the tapered portion of the plug can have a conical shape that is tapered at a constant angle; wherein the tapered portion of the plug is tapered at an angle A1 that is 12.5 degrees (or approximately 12.5 degrees) relative to the longitudinal axis A of the plug; wherein the tapered portion of the plug is tapered at an angle A1 that is from 6 degrees (or approximately 6 degrees) or less to 30 degrees (or approximately 30 degrees) or more, or from 8 degrees (or approximately 8 degrees) to 20 degrees (or approximately 20 degrees), or from 10 degrees (or approximately 10 degrees) to 15 degrees (or approximately 15 degrees) relative to the longitudinal axis A of the plug; wherein the rounded distal tip can have a radius R1 of 0.13 mm, or from 0.05 mm (or approximately 0.05 mm) or less to 0.25 mm (or approximately 0.25 mm) or more, or from 0.1 mm (or approximately 0.1 mm) to 0.15 mm (or approximately 0.15 mm), or of any values within any of the foregoing ranges or from and to any values within the foregoing ranges; wherein a transition from the body portion to the tapered portion is rounded; and/or wherein a transition from the body portion to the tapered portion is rounded and can have a radius R2 of 0.05 mm, or from 0.03 mm (or approximately 0.03 mm) or less to 0.1 mm (or approximately 0.1 mm) or more, or from 0.06 mm (or approximately 0.06 mm) to 0.08 mm (or approximately 0.08 mm), or of any values within any of the foregoing ranges or from and to any values within the foregoing ranges.

Further, any embodiments of the devices, kits, and methods disclosed herein can include, in additional embodiments, one or more of the following features, components, and/or details, in any combination with any of the other features, components, and/or details of any other embodiments disclosed herein: wherein the plug can have an overall length L1 of 2.0 mm (or approximately 2.0 mm); wherein the plug can have an overall length L1 of from 1.5 mm (or approximately 1.5 mm) or less to 3.0 mm (or approximately 3.0 mm) or more, or from 1.7 mm (or approximately 1.7 mm) to 2.4 mm (or approximately 2.4 mm), or of any values within any of the foregoing ranges or from and to any values within the foregoing ranges; wherein the tapered portion of the plug can have a length L2 of 0.9 mm (or approximately 0.9 mm); wherein the tapered portion of the plug can have a length L2 of from 0.7 mm (or approximately 0.7 mm) or less to 1.3 mm (or approximately 1.3 mm) or more, or from 0.8 mm (or approximately 0.8 mm) to 1.1 mm (or approximately 1.1 mm), or of any values within any of the foregoing ranges or from and to any values within the foregoing ranges; wherein the body portion of the plug can have a length L3 of 1.1 mm (or approximately 1.1 mm); and/or wherein the body portion of the plug can have a length L3 of 0.8 mm (or approximately 0.8 mm) or less to 1.7 mm (or approximately 1.7 mm) or more, or from 0.9 mm (or approximately 0.9 mm) to 1.3 mm (or approximately 1.3 mm), or of any values within any of the foregoing ranges or from and to any values within the foregoing ranges.

Material:

Further, any embodiments of the devices, kits, and methods disclosed herein can include, in additional embodiments, one or more of the following features, components, and/or details, in any combination with any of the other features, components, and/or details of any other embodiments disclosed herein: wherein the plug is constructed from a polymer material; wherein the plug is constructed from a biodegradable material; wherein the biodegradable material is selected from polymers or copolymers made in whole or in part, from glycolide, lactide, ρ-dioxanone, ε-caprolactone, trimethylene carbonate, or other biodegradable monomers; wherein the plug is configured to degrade over time in the body so as to no longer be capable of blocking flow through the lacrimal drainage system; wherein the plug is configured to degrade in the body within a period of time from a few days to approximately 12 months or longer, or from approximately 2 months to approximately 6 months; wherein the plug is made from a flexible material; and/or wherein the plug is sterile.

DETAILED DESCRIPTION OF SOME EXEMPLIFYING EMBODIMENTS

Described herein are embodiments of novel plug devices for occluding the canaliculi, for example and without limitation, for occluding or substantially occluding at least the vertical canaliculi, of the lacrimal drainage system.

In some embodiments, the plug devices 100 (also referred to herein as plugs) for occluding the lacrimal drainage system L can have a body portion 102 having a first end 104 and a second end 106, a tapered portion 110 extending away from the second end 106 of the body portion 102, and a distal tip 114. In any embodiments disclosed herein, the distal tip 114 can be rounded and/or the body portion 102 can have a continuous cylindrical shape between the first end 104 and the second end 106 thereof. In some embodiments, the first end 104 can be flat or planar (or approximately flat or planar) and/or can be orthogonal (or approximately orthogonal) to a longitudinal axis A of the plug 100. In other embodiments, the first end 104 can be rounded or curved, or have any other desirable shape. For example, the first end 104 can have an approximately spherical surface.

Any embodiments of the plug device 100 can have a shape that is symmetrical about a longitudinal axis A of the plug device 100. Further, some embodiments of the plug device 100 can have a smooth and continuous surface along the entire body portion thereof, without recesses, depressions, channels, or other inwardly projecting surfaces or features that project inwardly from the outside surface of the body portion. Similarly, some embodiments of the plug device 100 can have a smooth and continuous surface along the entire body portion thereof, without projections, ribs, rings, sharp edges or other outwardly projecting surfaces or features that project outwardly from the outside surface of the body portion. In some embodiments, the outside surface of the body portion, which can be cylindrically shaped, can define an outermost surface of the plug device and/or an innermost surface of the plug device. Other embodiments of the plug device 100 can have recesses, depressions, channels, surface texture or other surface features, or other inwardly projecting surfaces or features that project inwardly from the outside surface of the body portion. In some embodiments, these features can be used for plug devices that are configured for drug eluding applications.

Figure 1:
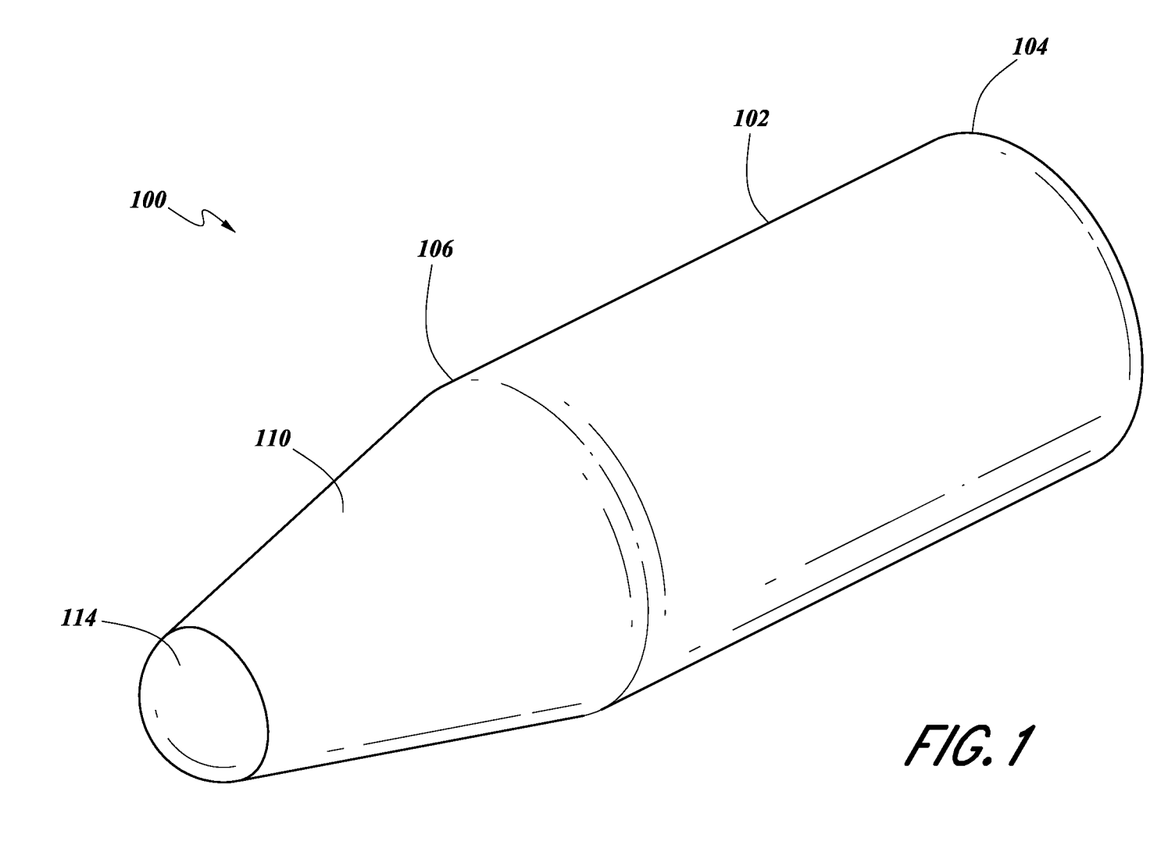
FIG. 1 is a perspective view showing a front and top of an embodiment of a plug device for occluding the lacrimal drainage system.
Figure 2:
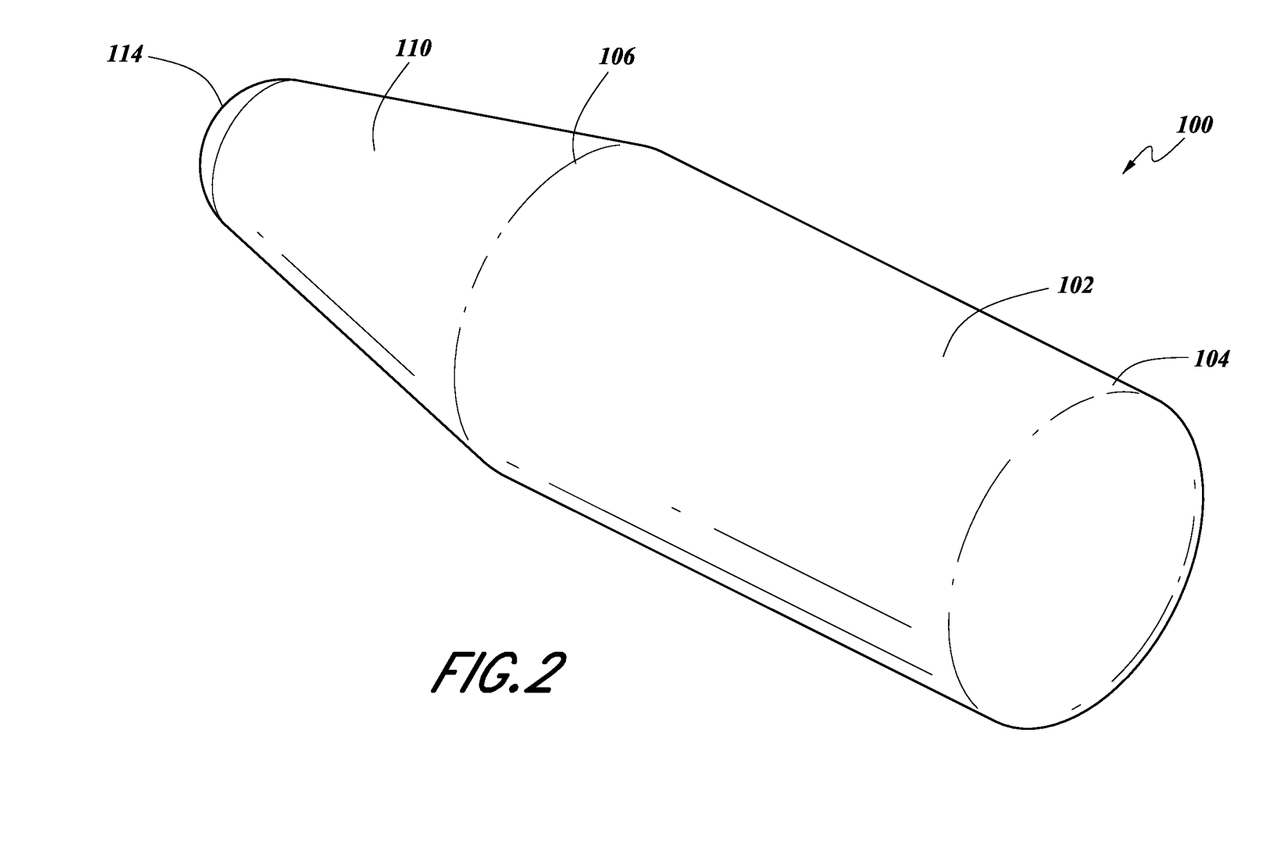
FIG. 2 is a second perspective view of the embodiment of the plug device of FIG. 1, showing the back and bottom of the plug device.
Figure 3:
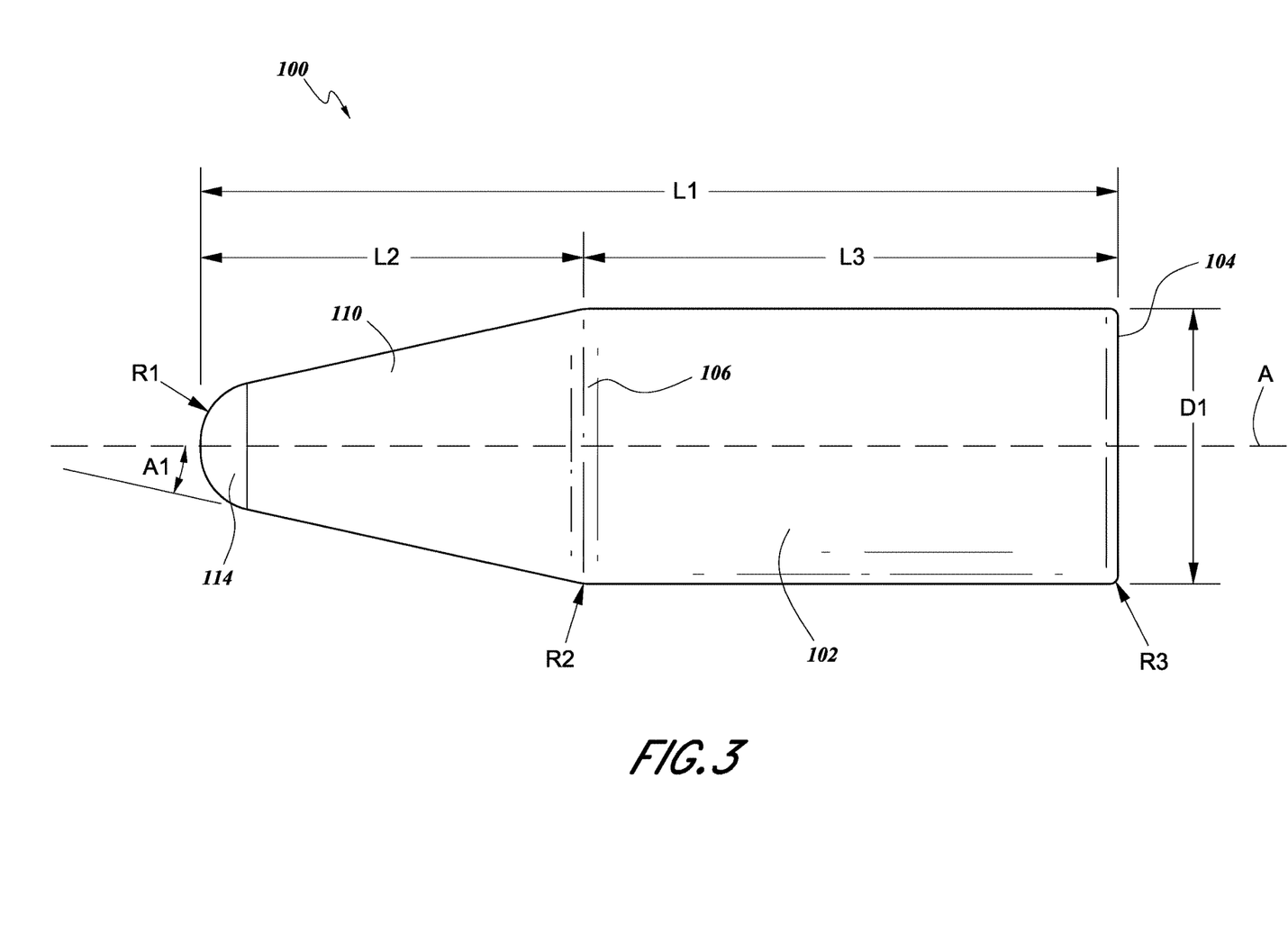
FIG. 3 shows a side view of the embodiment of the plug device of FIG. 1.
Figures 4, 5:
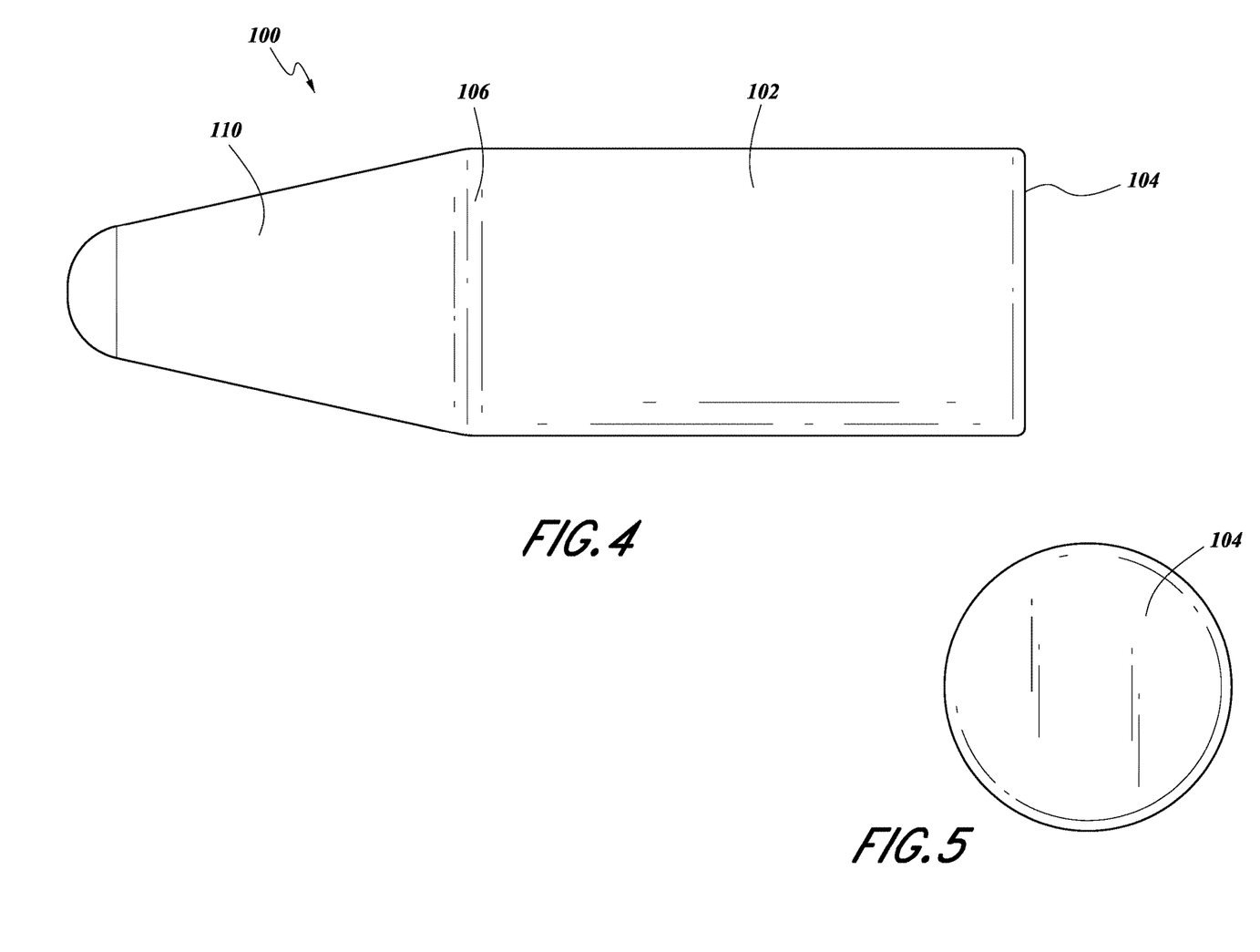
FIG. 4 shows another side view of the embodiment of the plug device of FIG. 1.
FIG. 5 shows a back end view of the embodiment of the plug device of FIG. 1, showing a first end of the plug device of FIG. 1.

Size:

With reference to FIG. 3, some embodiments of the plug 100 can have an overall length L1 of 2.0 mm (or approximately 2.0 mm), or an overall length L1 of from 1.5 mm (or approximately 1.5 mm) or less to 3.0 mm (or approximately 3.0 mm) or more, or from 1.7 mm (or approximately 1.7 mm) to 2.4 mm (or approximately 2.4 mm), or of any values within any of the foregoing ranges or from and to any values within the foregoing ranges. Further, in some embodiments, the tapered portion 110 of the plug 100 can have a length L2 of 0.9 mm (or approximately 0.9 mm), or a length L2 of from 0.7 mm (or approximately 0.7 mm) or less to 1.3 mm (or approximately 1.3 mm) or more, or from 0.8 mm (or approximately 0.8 mm) to 1.1 mm (or approximately 1.1 mm), or of any values within any of the foregoing ranges or from and to any values within the foregoing ranges. Further, some embodiments of the plug 100 can have a length L3 of the body portion 102 of 1.1 mm (or approximately 1.1 mm), or a length L3 of from 0.8 mm (or approximately 0.8 mm) or less to 1.7 mm (or approximately 1.7 mm) or more, or from 0.9 mm (or approximately 0.9 mm) to 1.3 mm (or approximately 1.3 mm), or of any values within any of the foregoing ranges or from and to any values within the foregoing ranges. Advantageously, the overall length L1 of the plug 100 can generally correspond to a length of the vertical canaliculus V into which the plug 100 can be inserted.

Some embodiments of the plug 100 (for example and without limitation, a single plug size) can be sized and configured to be inserted through a wide range of human punctal opening sizes to occlude a human canaliculus. Some embodiments of the plug 100 (for example and without limitation, a single plug size) can be sized and configured to be inserted through any and all human punctal opening sizes and occlude any and all human vertical canaliculus sizes, or any and all human horizontal canaliculus sizes. For example and without limitation, any embodiments of the plug 100 disclosed herein can be configured to be inserted through a punctal opening having a diameter of from 0.2 mm (or approximately 0.2 mm) or less to 1.0 mm (or approximately 1.0 mm) or more. For example and without limitation, in some embodiments, the body portion 102 of the plug 100 can have a diameter D1 of 0.6 mm (or approximately 0.6 mm), or a diameter D1 of from 0.3 mm (or approximately 0.3 mm) or less to 0.9 mm (or approximately 0.9 mm) or more, or from 0.5 mm (or approximately 0.5 mm) to 0.7 mm (or approximately 0.7 mm), or of any values within any of the foregoing ranges or from and to any values within the foregoing ranges.

In any embodiments of the plug 100 disclosed herein, the tapered portion 110 can be configured such that a size or diameter of the plug 100 decreases from the second end 106 of the body portion 102 to the distal tip 114. In some embodiments, the tapered portion 110 of the plug 100 can have a conical shape that can be tapered at a constant angle (e.g., can have a wall profile that can be linear or approximately linear). The tapered portion 110 of the plug 100 can be tapered at an angle A1 that is 12.5 degrees (or approximately 12.5 degrees) relative to the longitudinal axis A of the plug 100, or can be tapered at an angle A1 that is from 6 degrees (or approximately 6 degrees) or less to 30 degrees (or approximately 30 degrees) or more, that is from 8 degrees (or approximately 8 degrees) to 20 degrees (or approximately 20 degrees), or from 10 degrees (or approximately 10 degrees) to 15 degrees (or approximately 15 degrees) relative to the longitudinal axis A of the plug 100. In some embodiments, the tapered portion 110 can have a wall profile that is curved, for example and without limitation, convexly or concavely.

In some embodiments, the distal tip 114 can have a radius R1 of 0.13 mm, or from 0.05 mm (or approximately 0.05 mm) or less to 0.25 mm (or approximately 0.25 mm) or more, or from 0.1 mm (or approximately 0.1 mm) to 0.15 mm (or approximately 0.15 mm), or of any values within any of the foregoing ranges or from and to any values within the foregoing ranges. Further, the transition from the body portion 102 to the tapered portion 110 can be abrupt or can be rounded.

Material:

The plug 100 of any embodiments disclosed herein can be made from any suitable or desired material. Some embodiments of the plug 100 can be bioabsorbable, dissolvable, or degradable in the body. Some embodiments of the plug can be configured to gradually break down and be absorbed by the body. In some embodiments, the plug 100 can be made from natural materials, such as collagen, for example and without limitation. In some embodiments, the plug 100 can be made from polydioxanone, or from a biodegradable polymers or copolymers made, in whole or in part, from glycolide, lactide, ρ-dioxanone, ε-caprolactone, trimethylene carbonate, or other biodegradable monomers without limitation, or from any other suitable or desired material. The plugs can be configured to last in the canaliculus from a few days to one or more months and can be used to keep the eye moist after having particular types of surgery, or when a user wishes to try plugs for a short period of time, or to use plugs to elude a substance into the canaliculus. In some embodiments, the plug 100 can be configured to degrade in the body, so as to no longer be capable of blocking flow through the lacrimal drainage system, within a period of a few days to approximately 12 months or longer, or from approximately 2 months to approximately 6 months. Other embodiments can be made for a longer lasting or permanent implantation or use. For example and without limitation, any embodiments disclosed herein can be made from a medical grade plastic material, or silicone elastomer. These plugs can be configured to stay in the permanently until manually removed.

In some embodiments, the plug 100 and/or any portions of the device used to implant the plug can be sterile.

Figure 6:
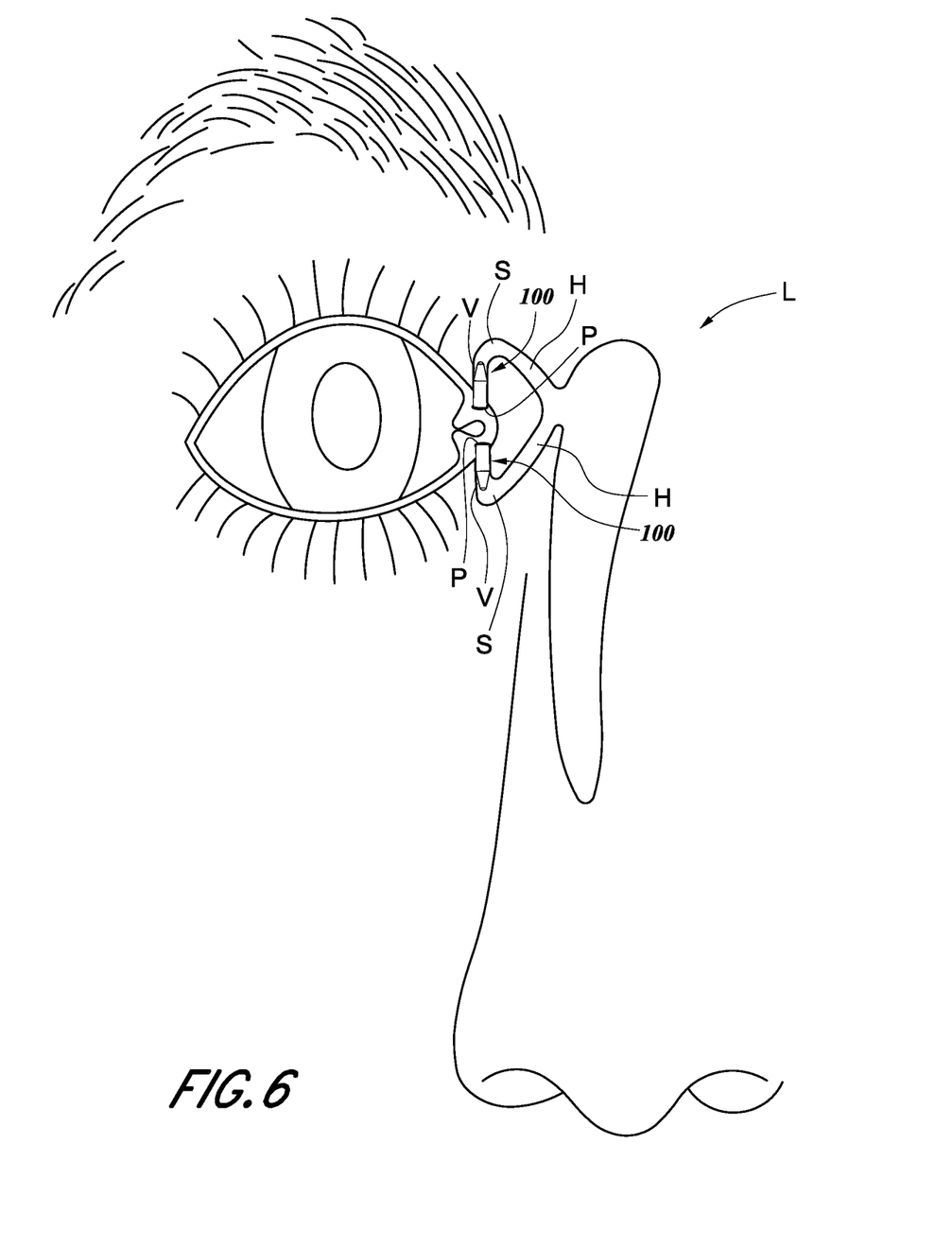
FIG. 6 shows a first and a second plug device positioned in a first vertical canaliculus and a second vertical canaliculus, respectively, of a lacrimal drainage system of a patient.
Figure 7:
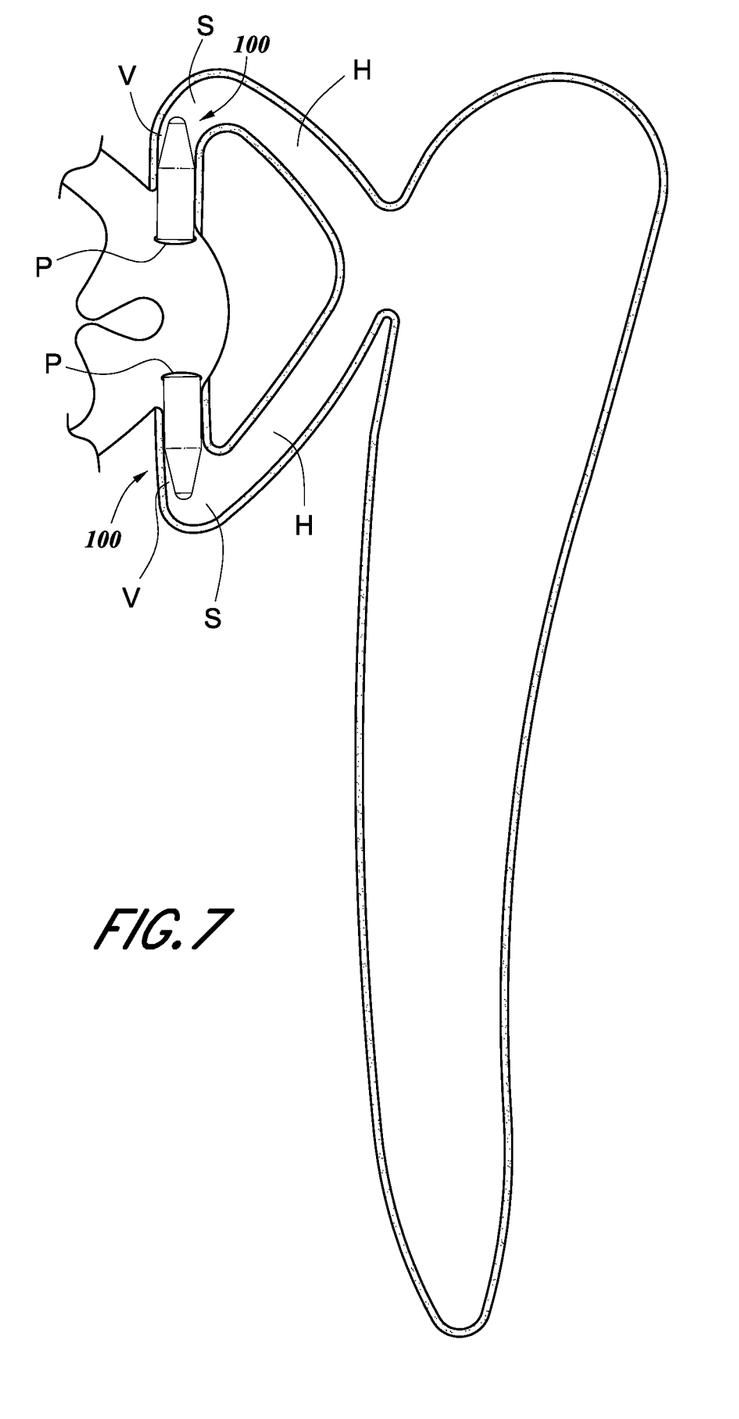
FIG. 7 shows an enlarged view of a portion of FIG. 6.
Figure 8:
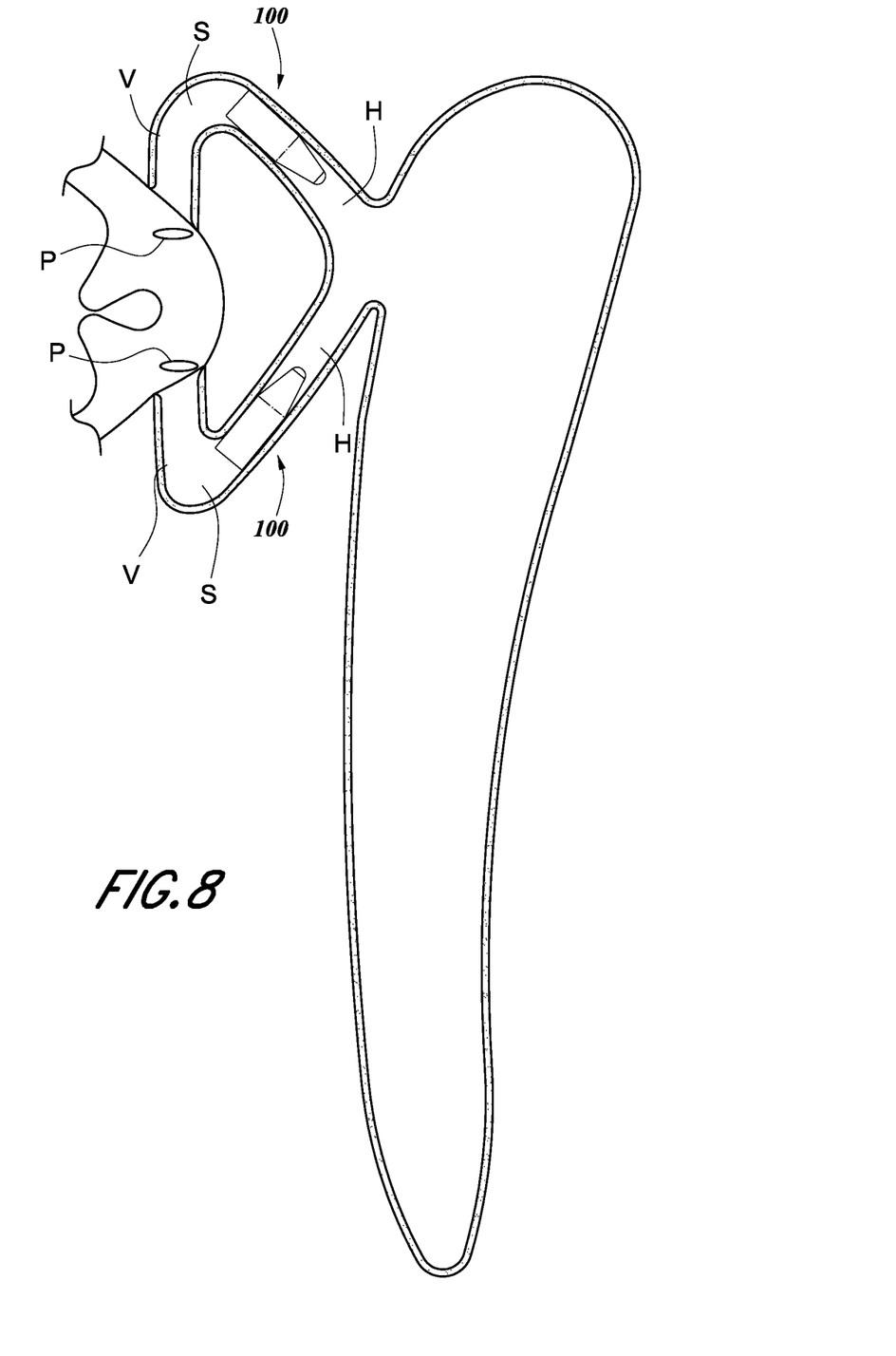
FIG. 8 shows a first and a second plug device positioned in a first horizontal canaliculus and a second horizontal canaliculus, respectively, of a lacrimal drainage system of a patient.

Occlusion of the Vertical and Horizontal Canaliculi:

With reference to FIGS. 6 and 7, some embodiments of the plug 100 can be sized and configured to occlude a vertical canaliculus V of the lacrimal drainage system L. For example and without limitation, the plug 100 can be configured to be inserted completely within the vertical canaliculus V of the lacrimal drainage system L so that no portion of the plug 100 extends outside of the vertical canaliculus V. Accordingly, the plug 100 can be inserted completely within the vertical canaliculus V of the lacrimal drainage system L so that no portion of the plug 100 and/or so that no portion of a body portion 102 extends back through the punctal opening P and/or so that no portion of the tapered portion 110 extends into the horizontal canaliculus H. The plug 100 can be configured such that the distal tip 114 can be inserted into the punctal opening P first. The tapered portion 110 can facilitate the insertion of the plug 100 through the punctal opening P (e.g., irrespective of the size of the punctal opening P, the tapered portion 110 can dilate or increase the diameter of the punctal opening P during insertion) into the vertical canaliculus V. The plug 100 can be a one-size-fits-all plug that can be implanted through a punctal opening P of different sizes. Some embodiments of the method of implanting a plug 100 or of occluding a lacrimal drainage system can include advancing a plug 100 into a first vertical canaliculus V of the lacrimal drainage system L without advancing any portion of the plug 100 into a horizontal canaliculus H of the lacrimal drainage system L, or so that no portion of the plug 100 extends back through the punctal opening P of the lacrimal drainage system.

In some embodiments, the plug 100 can be advanced through the punctal opening P and into the vertical canaliculus V so that the first end 104 of the plug 100 is flush with punctal opening P, or so that the first end 104 of the plug 100 is advanced past the punctal opening P so that the first end 104 of the plug 100 is within the vertical canaliculus and not extending out of the vertical canaliculus. This can reduce the risk of the plug 100 becoming inadvertently removed after implantation, such as by rubbing or scratching the eye in the region of the plug 100 and/or other discomfort related to the plug device extending out of the tear duct. In some embodiments, the plug 100 can be advanced through the punctal opening P and the vertical canaliculus V, into the horizontal canaliculus H of the lacrimal drainage system L so that no portion of the plug 100 extends outside of the horizontal canaliculus H.

Kit:

Also disclosed herein are embodiments of a kit for occluding an upper punctum or tear duct and a lower punctum or tear duct, including a first plug 100 having any of the features, sizes, and/or other details of any of the plug device embodiments disclosed herein in combination with or in place of any of the other features, sizes, and/or other details disclosed below, and a second plug 100 having any of the features, sizes, and/or other details of any of the plug device embodiments disclosed herein in combination with or in place of any of the other features, sizes, and/or other details disclosed below. The first plug 100 can have a body portion 102 and a tapered portion 110 projecting from the body portion of the first plug in an axial direction. The body portion 102 can have a continuous cylindrical outer surface between a first end 104 and a second end 106 thereof, and the outer surface can have a first diameter. The second plug 100 (or any number of additional plugs) can have a body portion 102 and a tapered portion 110 projecting from the body portion of the second plug in an axial direction. The second plug 100 can have a continuous cylindrical outer surface between a first end 104 and a second end 106 of the body portion 102 of the second plug 100. The body portion 102 or outer surface of the body portion 102 of the second plug can have a second diameter.

In some embodiments, a diameter or a cross-sectional size of the second plug 100 (for example and without limitation, of the body portion 102 of the second plug 100) can be different than a diameter or a cross-sectional size of the first plug 100 (for example and without limitation, of the body portion 102 of the first plug 100). In some embodiments, the second diameter or cross-sectional size of the second plug 100, or the body portion 102 of the second plug 100, can be less than the first diameter or cross-sectional size of the first plug 100, or of the body portion 102 of the first plug 102. Or, in some embodiments, the second diameter or cross-sectional size of the second plug or the body portion thereof can be greater than the first size or diameter of the first plug or the body portion thereof. The kit can, in some embodiments, include any number of different sized plugs to treat a wide range of tear duct sizes. Additionally, in some embodiments of the kit, the first plug can be removably coupled with (e.g., pre-coupled with) a first implantation device and the second plug can be removably coupled with (e.g., pre-coupled with) a second implantation device.

Method:

Described below are methods and steps of methods of occluding a lacrimal drainage system L that can be used with any of the embodiments of the plug device 100 that are disclosed herein and/or other methods of implanting one or more plugs 100 of any of the embodiments disclosed herein. In some embodiments, a plug 100 (which can be a first plug) can be advanced through a first punctal opening P of the lacrimal drainage system L. The plug 100 can be advanced into a first vertical canaliculus V of the lacrimal drainage system L, without advancing any portion of the first plug 100, and/or any portion of the body portion 102 of the first plug 100, into a horizontal canaliculus H of the lacrimal drainage system L, or extend back through the punctal opening P of the lacrimal drainage system L. In any embodiments, the plug 100 can have any of the features, sizes, and/or other details of any of the plug device embodiments disclosed herein in combination with or in place of any of the features, sizes, and/or other details disclosed below. In some embodiments, the first plug 100 can have a body portion 102 having a first end 104 and a second end 106, and a tapered portion 110 extending away from the second end 106 of the body portion 102. Further, the body portion 102 can have a continuous cylindrical shape between the first end 104 and the second end 106 thereof.

In some embodiments, the method of occluding a lacrimal drainage system L can further include advancing a second plug 100 through a second punctal opening P of the lacrimal drainage system L. In any embodiments, the second plug 100 can have any of the features, sizes, and/or other details of any of the plug device embodiments disclosed herein in combination with or in place of any of the features, sizes, and/or other details disclosed below. Some embodiments of the method can further include advancing the second plug 100 into a second vertical canaliculus V of the lacrimal drainage system L, without advancing any portion of the second plug 100, or any portion of the body portion 102 of the second plug 100, into a horizontal canaliculus H of the lacrimal drainage system L, or extend back through the punctal opening P of the lacrimal drainage system L. In some embodiments, this can ensure that the first and/or second plugs can be reached and retrieved from the tear ducts, as needed or desired. Further, the first and second plug devices can be inserted into the tear duct of the user or patient without any portion of the plug device extending out of the tear duct.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A plug configured for occluding a vertical canaliculus of a lacrimal drainage system, comprising:
    a body portion having a first end and a second end, wherein the first end of the body portion is coincident with a first terminal end of the plug and extends to the second end of the body portion;
    a tapered portion coincident to and extending away from the second end of the body portion at a proximal end of the tapered portion, the tapered portion having a conical shape; and
    a distal tip;
    wherein:
        the plug has a continuous cylindrical shape in a preimplantation state between the first terminal end of the plug and the second end of the body portion, the body portion having a constant outer diameter from the first terminal end to the second end;
        the proximal end of the tapered portion has an outer diameter;
        the second end of the body portion has an outer diameter that is same as the outer diameter of the proximal end of the tapered portion;
        the tapered portion decreases in diameter from the second end of the body portion and the proximal end of the tapered portion along a length of the tapered portion toward the distal tip, the diameter of the tapered portion from the proximal end to the distal tip is equal to or less than the constant outer diameter of the body portion;
        the plug is configured to be, after complete implantation into the lacrimal drainage system, completely and entirely positioned within the vertical canaliculus of the lacrimal drainage system without advancing any portion of the body portion of the plug into a horizontal canaliculus of the lacrimal drainage system to occlude a flow through the lacrimal drainage system, the plug has an overall length between 1.5 mm and 2.5 mm such that the plug does not extend out of the vertical canaliculus or into the horizontal canaliculus after complete implantation;
        the plug is solid along the overall length of the plug;
        the plug is completely bioabsorbable, dissolvable, or degradable in the vertical canaliculus within a period of time from 3 months to 12 months; and
        the plug is made from lactide, ρ-dioxanone, ε-caprolactone, or trimethylene carbonate.

2. The plug of claim 1, wherein the first end is planar and is orthogonal to a longitudinal axis A of the plug.

3. The plug of claim 1, wherein the distal tip is rounded.

4. The plug of claim 1, wherein the plug is sized and configured to be inserted through a punctal opening having a diameter ranging from 0.2 mm to 1.0 mm.

5. The plug of claim 1, wherein the length of the tapered portion of the plug is between 0.7 mm to 1.3 mm.

6. The plug of claim 1, wherein the body portion of the plug has a diameter D1 between 0.3 mm to 0.9 mm.

7. The plug of claim 1, wherein the tapered portion of the plug has the conical shape that is tapered at a constant angle.

8. The plug of claim 1, wherein the tapered portion of the plug is tapered at an angle A1 that is from 6 degrees to 30 degrees relative to a longitudinal axis A of the plug.

9. The plug of claim 1, wherein the plug is bioabsorbable, dissolvable, or degradable in a body within a period of 3 months to 6 months.

10. The plug of claim 1, wherein the plug is bioabsorbable, dissolvable, or degradable in a body within a period of 6 months to 12 months.

11. A method of occluding a vertical canaliculus of a lacrimal drainage system, comprising:
    advancing a first plug through a first punctum of the lacrimal drainage system, the first plug having:
        a body portion having a first end and a second end, wherein the first end of the body portion is coincident with a first terminal end of the first plug and extends to the second end of the body portion, the body portion having a constant outer diameter from the first terminal end to the second end, the first plug having an overall length between 1.5 mm and 2.5 mm; and
        a tapered portion coincident to and extending away from the second end of the body portion at a proximal end of the tapered portion, the tapered portion having a conical shape, the tapered portion decreasing in diameter from the second end of the body portion and the proximal end of the tapered portion along a length of the tapered portion toward a distal tip, the diameter of the tapered portion from the proximal end of the tapered portion to the distal tip is equal to or less than the constant outer diameter of the body portion;
    wherein the proximal end of the tapered portion has an outer diameter and the second end of the body portion has an outer diameter that is same as the outer diameter of the proximal end of the tapered portion;
    wherein the first plug has a continuous cylindrical shape in a preimplantation state between the first terminal end of the first plug and the second end of the body portion;
    wherein the first plug is made from lactide, ρ-dioxanone, ε-caprolactone, or trimethylene carbonate and is solid along the overall length of the first plug; and
    advancing the first plug completely into the vertical canaliculus of the lacrimal drainage system without advancing any portion of the first plug into a horizontal canaliculus of the lacrimal drainage system; and retaining the first plug entirely within the vertical canaliculus without advancing any portion of the first plug into the horizontal canaliculus;

wherein the first plug is completely bioabsorbable, dissolvable, or degradable in the vertical canaliculus within a period of time of 3 months to 12 months to no longer occlude the vertical canaliculus of the lacrimal drainage system.

12. The method of claim 11, wherein the length of the tapered portion of the first plug is between 0.7 mm to 1.3 mm.

13. The method of claim 11, wherein the body portion of the first plug has a diameter D1 between 0.3 mm to 0.9 mm.

14. The method of claim 11, wherein the tapered portion of the first plug has the conical shape that is tapered at a constant angle.

15. The method of claim 11, wherein the tapered portion of the first plug is tapered at an angle A1 that is from 6 degrees to 30 degrees relative to a longitudinal axis A of the first plug.

16. A kit for occluding a first vertical canaliculus and a second vertical canaliculus of a lacrimal drainage system, comprising:
a first plug configured to be positioned in the first vertical canaliculus, comprising:
a body portion having a continuous cylindrical outer surface in a preimplantation state between a first end and a second end thereof, the continuous cylindrical outer surface having a constant first diameter, wherein the first end of the body portion of the first plug is coincident with a first terminal end of the first plug and extends to the second end of the body portion; and
a tapered portion projecting from the second end of the body portion of the first plug at a proximal end of the tapered portion in an axial direction;
wherein:
the tapered portion of the first plug decreases in diameter from the second end of the body portion of the first plug and the proximal end of the tapered portion of the first plug along a length of the tapered portion toward a distal tip;
the diameter of the tapered portion from the proximal end to the distal tip of the first plug is equal to or less than the constant first diameter of the body portion of the first plug;
the second end of the body portion of the first plug has an outer diameter equal to an outer diameter of the proximal end of the tapered portion of the first plug; and
the first plug is configured to be, after complete implantation into a lacrimal drainage system, completely and entirely positioned within the first vertical canaliculus of the lacrimal drainage system to occlude a flow through the first vertical canaliculus without advancing any portion of the body portion of the first plug into a first horizontal canaliculus of the lacrimal drainage system;
a second plug configured to be positioned in the second vertical canaliculus, comprising:
a body portion having a continuous cylindrical outer surface in a preimplantation state between a first end and a second end thereof, the continuous cylindrical outer surface having a constant second diameter, wherein the first end of the body portion of the second plug is coincident with a first terminal end of the second plug and extends to the second end of the body portion of the second plug; and
a tapered portion projecting from the second end of the body portion of the second plug at a proximal end of the tapered portion in an axial direction;
wherein:
the tapered portion of the second plug decreases in diameter from the second end of the body portion of the second plug and the proximal end of the tapered portion of the second plug along a length of the tapered portion toward a distal tip;
the diameter of the tapered portion from the proximal end to the distal tip of the second plug is equal to or less than the constant second diameter of the body portion of the second plug;
the second end of the body portion of the second plug has an outer diameter equal to an outer diameter of the proximal end of the tapered portion of the second plug;
the second plug is configured to be, after complete implantation into a lacrimal drainage system, completely and entirely positioned within the second vertical canaliculus of the lacrimal drainage system to occlude a flow through the lacrimal drainage system without advancing any portion of the body portion of the second plug into a second horizontal canaliculus of the lacrimal drainage system;
wherein:
the constant second diameter of the second plug is less than the constant first diameter of the first plug;
the first plug and the second plug each have an overall length between 1.5 mm and 2.5 mm such that each of the first plug and the second plug do not extend out of the first and second vertical canaliculus or into the first and second horizontal canaliculus, respectively, after complete implantation;
the first plug and the second plug are each completely bioabsorbable, dissolvable, or degradable in the first vertical canaliculus and the second vertical canaliculus, respectively, within a period of time from 3 months to 12 months;
the first plug and the second plug are made from lactide, ρ-dioxanone, ε-caprolactone, or trimethylene carbonate; and
the first plug and the second plug are each solid along an entire length thereof.

17. The kit of claim 16, wherein the first plug is removably coupled with a first insertion device and the second plug is removably coupled with a second insertion device.

* * * * *